Nov. 11, 1969 H. KERRIGAN Plant Pat. 2,939
AZALEA PLANT
Filed Jan. 16, 1968
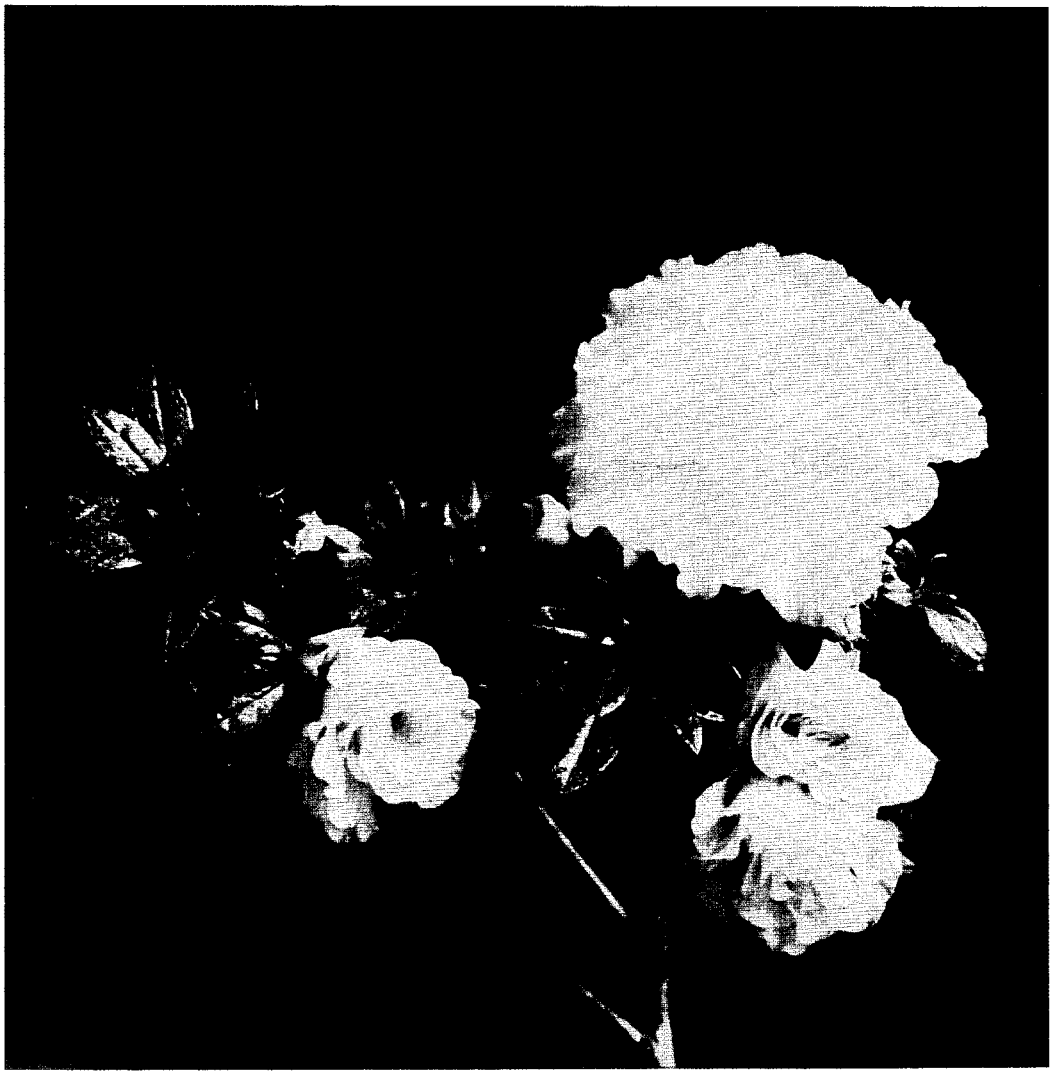

United States Patent Office

Plant Pat. 2,939
Patented Nov. 11, 1969

2,939
AZALEA PLANT

Howard Kerrigan, 3003 Tottterdell St.,
Oakland, Calif. 94611

Filed Jan. 16, 1968, Ser. No. 698,362
Int. Cl. A01h 5/02
U.S. Cl. Plt.—57 1 Claim The invention relates to a new and distinct variety of azalea plant of the Belgian indica type, originated by me in 1952 as a consequence of a breeding program begun in 1943. The parentage of my new azalea plant is as follows: L. C. Bobbink (P.P. 611 expired), the seed parent X Gables Rosebud (unpatented), the pollen parent.

The object of the cross was to produce a plant of compact habit, easy to propagate on its own roots, vigorous in growth habit, and with greater petalage than existing red azaleas in the trade.

These objectives were achieved along with other desirable improvements, as evidenced by the following unique combination of characteristics which are outstanding in the new variety and which distinguish it from its parents as well as from all other varieties of which I am aware. My new variety is primarily characterized by: The unique combination of very double ruffled flower of glowing red color, plant that propagates easily, grows rapidly, is vigorous yet densely compact, sets bud heavily all over the bush, blooms evenly when forced and retains the open flowers for a long period of time.

Asexual reproduction of my new variety by cuttings, through a series of annual propagations at Oakland and Santa Rosa, Calif., shows that all characteristics of the variety come true to form through succeeding propagations. The accompanying photographs illustrate the primary characteristics of my new variety as nearly true as is reasonably possible to make them with presently available techniques. The color references cited are those of the Horticultural Color Charts of the Royal Horticultural Society.

The following botanical description is based upon observation of my own rooted plants produced and grown under average conditions in greenhouses at Oakland and Santa Rosa Calif., from 1954 to 1967.

Large, robust, vigorous, densely compact plant spreading 24–36″ high with the same spread at maturity. Branches stout, but supple, gently arching. Basal shoots vigorous, about 3/32″ in diameter; axillary branches about 1/16″ the first season. Internodes of basal shoots between 1/8–5/8″ long. Stems erect to almost prostrate; rufous when young, becoming light green at the base and becoming rufous to gray-brown when old. Bark more or less conspicuously striate, young stems bearing prominent hyaline to chestnut strigae. The hyaline strigae being restricted to basal shoots and older wood; the chestnut strigae being found mainly on terminal growth.

Foliage evergreen, of two size classes. Leaves of vigorous growth about 7/8–1 1/4″ long x 3/8–1/2″ wide, petiolate, the petioles about 5/32″ long, lamina decurrent, descending the petiole up to 3/32″, elliptic. The margins are entire, somewhat ciliate, the cilia small, inconspicuous and chestnut in color. The apex is acute. The midrib is pubescent especially below. The trichomes are flat, lanceolate, slender up to 3/32″ in length, conspicuous, chestnut, abundant on lower surface, smaller and sparser on the upper surface of the midrib. The lamina is equally sparsely pubescent on both surfaces. Leaves of the branches of older or more mature wood smaller, about 1/2–7/8″ long by 1/4–3/8″ wide with proportionately smaller trichomes, but otherwise similar to the larger leaves. The color of the leaves is Spinach Green (HCC 0960) above and Spinach Green (HCC 0960/3) below.

The bud of the inflorescence is Lettuce Green (HCC 861). The scales are small, about 3/16″ wide x 7/16″ long, heart shaped to lanceolate, becoming cucullate at anthesis. Pubescence is moderate to heavy, small, golden brown, essentially restricted to the rib. The scales become scarious with sub-hyaline margins and green apices at dehiscence.

The inflorescents is 1–2 flowered. The flowers are borne in umbillate corymb. One flower of the 2 flowered inflorescence matures at the same time as or several days later than the more precocious one and has a slightly shorter peduncle.

Peduncles are short, slender 3/8–9/16″ long x 1/16″ thick, pubescent, light green, becoming somewhat pink where exposed to sunlight. Pubescence moderate to dense, hyaline to somewhat chestnut, where exposed to sunlight; short and silky. Calyx normal, five lobed, sepals entire. Tube of calyx about 1/8″ deep x 5/16″ across. Lobes about 1/8″ wide x 3/16″ long, ovate, not very variable as to shape and size. The margins of the lobes are long ciliate, as are the reverse, especially near the basal portion. The cilia are hyaline to chestnut (where exposed to sunlight and on older specimens). The color is Agathia Green (HCC 60/3) becoming Oxblood Red (HCC 00823/4) with age. The coralla is showy, China Rose (HCC 024/1) on both reverse and obverse. The obverse is maculate with Cardinal Red (HCC 822/2), the macullae are confined to the upper portion (the standard and two upper wings) of the coralla tube and the upper petals. The macullae are on the basal portion or lower 1/3 of the petals. The reverse of the coralla tube is streaked with white and lighter shades of Cardinal Red (HCC 822/2). The tube is about 1/2″ long x 5/8″ wide at the throat. Flaring, bilaterally symetrical, slightly gibbous, somewhat higher than broad, more or less prominently fluted with the midveins depressed. The five coralla lobes are of two size classes. The ventral two larger about 1–1 1/8″ across x 7/8–1″ deep, auriculate. The dorsal three lobes are smaller, about 7/8–1″ across x 7/8–1″ long. The lobes are occasionally incised. The margins of the sinus are auriculate, giving the impression that the coralla tube has between 5 and 8 lobes. The flower is about 2 1/8–2 1/4″ across x 1–1 1/4″ deep. The flower is completely double, all of the stamens having been transformed into petaloides. The petaloides (staminodes) are five in number, however 3 of these petaloides (staminodes) are lobed, giving the flower the appearance of having many more petalodia. The lobes number from 3 to 7 with some of the lobes being secondarily lobed. The petalodia (staminodia) range in size from 3/4″–7/8″ wide x 1 1/8–1 1/4″ long for those having no lobes to 1 1/2–2 1/2″ wide x 1 1/4–1 3/8″ long for those with lobes. The lobes measure 3/4–1 1/4″ wide x 15/16–1 1/8″ long.

The pistil is moderate in length about 1–1 1/4″. Stigma Ruby Red (HCC 827), capitate, twice as broad as style, 5 lobed, receptive surface divided into 5 sections, style slender, about 15/16–1 3/16″ long, sigmoid, expanded at base to nearly the diameter of the ovary, about 1/16″ in diameter at the base, 1/32″ at the middle. The thickened basal portion of the style pubescent, the pubescence long, silky, hyaline. Ovary about 1/8″ long x 3/32″ wide, heavily pubescent, the pubescence dense, long, silky and hyaline.

Having thus disclosed my invention, I claim:

1. A new and distinct variety of azalea plant of the Belgian indica type substantially as herein shown and described primarily characterized by: the unique combination of very double ruffled flower of glowing red color, plant that propagates easily, grows rapidly, is vigorous yet densely compact, sets bud heavily allover the bush, blooms evenly when forced and retains the open flowers for a long period of time.

No References Cited

ROBERT E. BAGWILL, Primary Examiner